US00PP28574P3

(12) United States Plant Patent
van den Haak

(10) Patent No.: US PP28,574 P3
(45) Date of Patent: Oct. 24, 2017

(54) *HEUCHERA* PLANT NAMED 'GOJIBERRY'

(50) Latin Name: *Heuchera×hybrida*
Varietal Denomination: Gojiberry

(71) Applicant: GOOTJES-ALLPLANT B.V., Schagen (NL)

(72) Inventor: Jelle van den Haak, Amsterdam (NL)

(73) Assignee: Gootjes-Allplant B.V., Schagen (NL)

( * ) Notice: Subject to any disclaimer, the term of this patent is extended or adjusted under 35 U.S.C. 154(b) by 49 days.

(21) Appl. No.: 14/998,593

(22) Filed: Jan. 23, 2016

(65) Prior Publication Data

US 2017/0215325 P1 Jul. 27, 2017

(51) Int. Cl.
*A01H 5/12* (2006.01)

(52) U.S. Cl.
USPC ..... Plt./440

(58) Field of Classification Search
USPC ..... Plt./440
See application file for complete search history.

*Primary Examiner* — June Hwu
(74) *Attorney, Agent, or Firm* — C. A. Whealy

(57) ABSTRACT

A new and distinct cultivar of *Heuchera* plant named 'Gojiberry', characterized by its compact and uniformly mounded plant habit; densely foliated and bushy appearance; reddish brown-colored leaves that with development become yellow orange in color; and good garden performance.

2 Drawing Sheets

Botanical designation: *Heuchera×hybrida.*
Cultivar denomination: 'GOJIBERRY'.

BACKGROUND OF THE INVENTION

The present invention relates to a new and distinct *Heuchera* plant of *Heuchera*, botanically known as *Heuchera×hybrida* and hereinafter referred to by the name 'Gojiberry'.

The objective of the breeding program is to create new compact *Heuchera* plants with attractive leaf colors with good garden performance.

The new *Heuchera* plant originated from a cross-pollination in April, 2010 in Heerhugowaard, The Netherlands of *Heuchera×hybrida* 'Crimson Curls', disclosed in U.S. Plant Pat. No. 13,729, as the female, or seed, parent with a proprietary selection of *Heuchera×hybrida* identified as code number 083-09-C005, not patented, as the male, or pollen, parent. The new *Heuchera* plant was discovered and selected by the Inventor as a single flowering plant within the progeny of the stated cross-pollination in a controlled greenhouse environment in Heerhugowaard, The Netherlands in July, 2011.

Asexual reproduction of the new *Heuchera* plant by tissue culture in controlled laboratory and greenhouse environments in Andijk, The Netherlands since March, 2013 has shown that the unique features of this new *Heuchera* plant are stable and reproduced true to type in successive generations.

SUMMARY OF THE INVENTION

The new *Heuchera* plant has not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Gojiberry'. These characteristics in combination distinguish 'Gojiberry' as a new and distinct *Heuchera* plant:

1. Compact and uniformly mounded plant habit.
2. Densely foliated and bushy appearance.
3. Reddish brown-colored leaves that with development become yellow orange in color.
4. Good garden performance.

Plants of the new *Heuchera* differ from plants of the female parent, 'Crimson Curls', in leaf color as plants of 'Crimson Curls' have dark purple brown and crimson-colored leaves. In addition, leaf margins of plants of the new *Heuchera* are not as undulate (curly) as leaf margins of 'Crimson Curls'.

Plants of the new *Heuchera* differ from plants of the male parent selection in leaf color as plants of the male parent selection have greenish yellow-colored leaves. In addition, leaf margins of plants of the new *Heuchera* are not as undulate (curly) as leaf margins of the male parent selection.

Plants of the new *Heuchera* can be compared to plants of the *Heuchera×hybrida* 'Peach Flambe', disclosed in U.S. Plant Pat. No. 17,195. In side-by-side comparisons, plants of the new *Heuchera* differ primarily from plants of 'Peach Flambe' in the following characteristics:

1. Plants of the new *Heuchera* are more vigorous than plants of 'Peach Flambe'.
2. Plants of the new *Heuchera* and 'Peach Flambe' differ in leaf color as plants of 'Peach Flambe' have rust to burgundy-colored leaves.

BRIEF DESCRIPTION OF THE PHOTOGRAPHS

The accompanying colored photographs illustrates the overall appearance of the new *Heuchera* plant showing the colors as true as it is reasonably possible to obtain in colored reproductions of this type. Colors in the photograph may differ slightly from the color values cited in the detailed botanical description which accurately describe the colors of the new *Heuchera* plant.

The photograph on the first sheet is a side perspective view of a typical flowering plant of 'Gojiberry' grown in a container.

The photograph at the top of the second sheet is a close-up view of a typical inflorescence of 'Gojiberry'.

The photograph at the bottom of the second sheet is a close-up view of typical leaves of 'Gojiberry'.

DETAILED BOTANICAL DESCRIPTION

The aforementioned photographs and following observations, measurements and values describe plants grown during the spring and early summer in 17-com containers in an outdoor nursery in Wieringerwerf, The Netherlands and under cultural practices typical of commercial *Heuchera* production. During the production of the plants, day temperatures ranged from 10° C. to 25° C. and night temperatures ranged from 4° C. to 15° C. Plants were 14 weeks old when the photographs and the description were taken. In the description, color references are made to The Royal Horticultural Society Colour Chart, 2007 Edition, except where general terms of ordinary dictionary significance are used.

Botanical classification: *Heucherax×hybrida* 'Gojiberry'.

Parentage:

*Female, or seed, parent.*—*Heucherax×hybrida* 'Crimson Curls', disclosed in U.S. Plant Pat. No. 13,729.

*Male, or pollen, parent.*—Proprietary selection of *Heucherax×hybrida* identified as code number 083-09-C005, not patented.

Propagation:

*Type.*—By tissue culture.

*Time to initiate roots, summer.*—About ten days at temperatures about 22° C.

*Time to initiate roots, winter.*—About 15 days at temperatures about 20° C.

*Time to produce a rooted young plant, summer.*—About 42 days at temperatures about 20° C.

*Time to produce a rooted young plant, winter.*—About 50 days at temperatures about 20° C.

*Root description.*—Fine, fibrous; typically light brown in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Herbaceous perennial; basal rosette plant habit with leaves developing from the base; densely foliated and dense and bushy appearance; compact and uniformly mounded plant habit; moderately vigorous growth habit.

*Plant height, soil level to top of foliar plane.*—About 23 cm.

*Plant height, soil level to top of inflorescences.*—About 49.5 cm.

*Plant diameter or spread.*—About 41 cm.

Leaf description:

*Quantity and arrangement.*—About 15 leaves per basal rosette; leaves, simple.

*Length.*—About 7.9 cm.

*Width.*—About 7.1 cm.

*Shape.*—Overall, broadly ovate; palmately lobed.

*Apex.*—Abruptly acute.

*Base.*—Hastate, lobes touching to moderately imbricate.

*Margin.*—Five to occasionally seven-lobed; crenate.

*Texture, upper surface.*—Pubescent.

*Texture, lower surface.*—Pubescent; pubescence more prominent along veins.

*Luster, upper surface.*—Matte.

*Luster, lower surface.*—Slightly glossy.

*Venation pattern.*—Palmate; reticulate.

*Color.*—Developing leaves, upper surface: Close to 176A and 178A. Developing leaves, lower surface: Close to 187C. Fully expanded leaves, upper surface: Close to 22B; fading to closer to 18A; venation, same as lamina color. Fully expanded leaves, lower surface: Close to between 22B and 23C tinged with close to 39B and 39C; venation, close to 150D.

*Petioles.*—Length: About 14.7 cm. Diameter: About 2 mm. Texture, upper and lower surfaces: Densely pubescent. Color, upper and lower surfaces: Close to 199B.

Flower description:

*Flower type and flowering habit.*—Single campanulate flowers arranged on compound spikes; each spike with about 265 flowers; about 1,600 flowers develop per plant during the flowering season; flowers face mostly outward to slightly drooping.

*Fragrance.*—None detected.

*Time of flowering.*—Plants flower continuously from the late spring into the summer in The Netherlands.

*Inflorescence longevity.*—Individual flowers last about one week on the plant; flowers not persistent.

*Inflorescence length.*—About 44.4 cm.

*Inflorescence width.*—About 6.7 cm.

*Flower diameter.*—About 5 mm.

*Flower depth (height).*—About 7 mm.

*Flower buds.*—Height: About 3 mm. Diameter: About 2 mm. Shape: Broadly ovate. Color: Close to N155C; towards the base, close to 158D and tinged with close to 62B.

*Petals.*—Quantity and arrangement: Five petals in a single whorl. Length: About 3 mm. Width: About 0.8 mm. Shape: Oblanceolate. Apex: Narrowly acute. Margin: Entire. Texture, upper and lower surfaces: Smooth, glabrous. Luster, upper and lower surfaces: Matte. Color: When opening, upper and lower surfaces: Lighter than NN155D. Fully opened, upper and lower surfaces: Lighter than NN155D.

*Sepals.*—Quantity and arrangement: Five sepals in a single whorl; fused at base. Length: About 4 mm. Width: About 1.5 mm. Shape: Roughly elliptic. Apex: Broadly acute. Margin: Entire. Texture, upper surface: Smooth. Texture lower surface: Densely pubescent. Color: When opening, upper surface: Close to 155A; central band, close to 15A to 15B. When opening, lower surface: Close to NN155A; towards the base, close to 155D; central band, close to 162D. Fully opened, upper surface: Close to 155A; distally, close to NN155B; central band, close to 15A to 15B. Fully opened, lower surface: Close to NN155A; towards the base, close to 155D; central band, close to 162D.

*Flower bracts.*—Quantity and arrangement: One subtending the calyx. Length: Less than 1 mm. Width:

Less than 1 mm. Color, upper and lower surfaces: Close to 183C tinged with close to 199B.

*Peduncles*.—Length, primary: About 43.9 cm. Length, lateral: About 0.4 cm to 5.4 cm. Diameter, primary: About 3.5 mm. Diameter, lateral: About 1 mm. Strength: Moderately strong. Aspect, primary: Mostly erect. Aspect, lateral: About 55° from primary peduncles. Texture: Pubescent. Color: Close to 183C; with development, tinged with close to 199B.

*Pedicels*.—Length: About 3.5 mm. Diameter: About 0.5 mm. Strength: Moderately strong. Color: Close to 183D; distally, close to 155D.

*Reproductive organs*.—Androecium: Stamen number: Five per flower. Filament length: About 3.5 mm. Filament color: Close to NN155D. Anther length: About 0.5 mm. Anther shape: Deltoid. Anther color: Close to 24A. Amount of pollen: Moderate. Pollen color: Close to 10B to 10C. Gynoecium: Pistil number: Two per flower. Pistil length: About 4 mm. Stigma shape: Pointed. Stigma color: Close to N155D. Style length: About 3.75 mm. Style color: Close to NN155D. Ovary color: Close to 155A to 155B.

*Seeds and fruits*.—Seed and fruit development have not been observed on plants of the new *Heuchera*.

Pathogen & pest resistance: Resistance to pathogens and pests has not been observed on plants of the new *Heuchera* grown under commercial conditions.

Garden performance: Plants of the new *Heuchera* have been observed to have good garden performance and to tolerate high temperatures about 35° C. and to be hardy to USDA Hardiness Zone 3.

It is claimed:

1. A new and distinct *Heuchera* plant named 'Gojiberry' as illustrated and described.

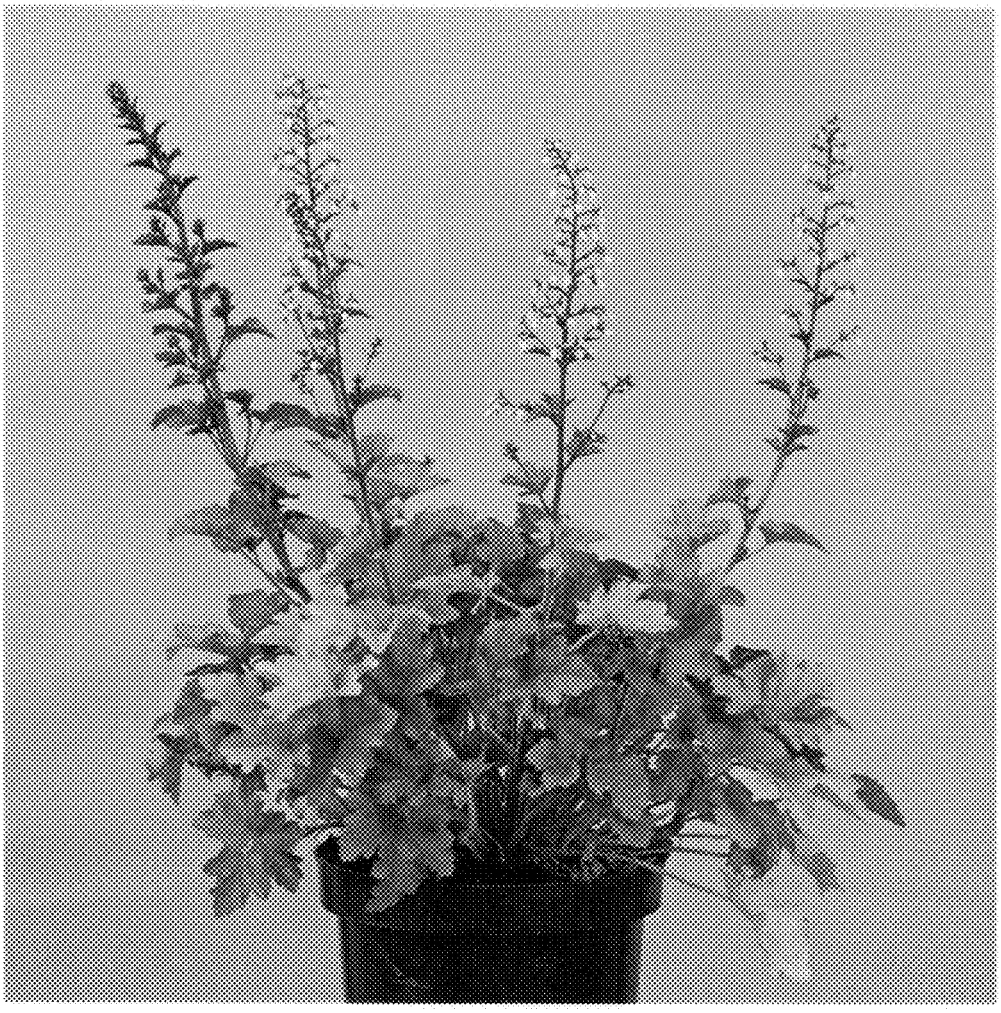

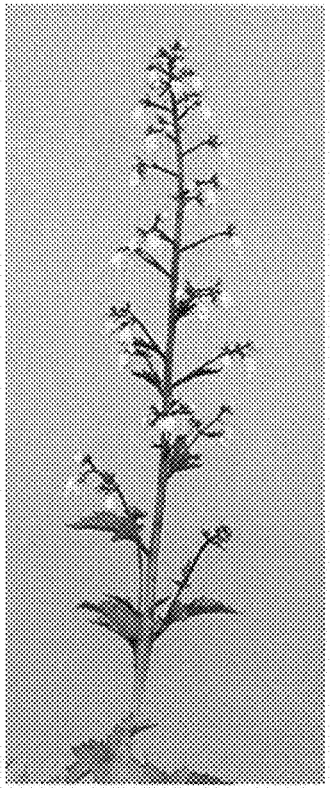
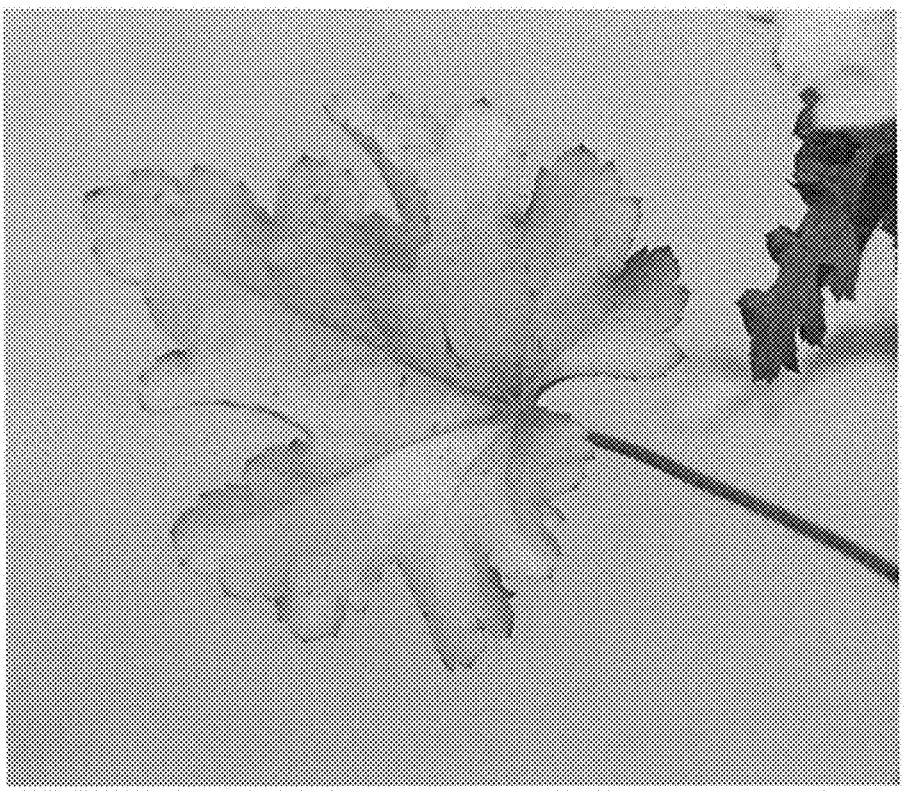

* * * * *